United States Patent [19]

De Paoli et al.

[11] Patent Number: 5,534,268

[45] Date of Patent: Jul. 9, 1996

[54] LIPOSOMES CONTAINING BIOAVAILABLE IRON (II) AND PROCESS FOR OBTAINING THEM

[75] Inventors: Tomás De Paoli, Ramos Mejía; Alfredo A. Hager, Villa Adelina, both of Argentina

[73] Assignees: Juan Carlos Ferroni, Lujan; Lipotech S.A., Buenos Aires, both of Argentina

[21] Appl. No.: 264,974

[22] Filed: Jun. 24, 1994

[30] Foreign Application Priority Data

Nov. 9, 1993 [AR] Argentina .................................. 326.541

[51] Int. Cl.⁶ ..................................................... A61K 9/127
[52] U.S. Cl. ............................. 424/450; 424/428; 426/89; 426/98; 426/99; 426/100
[58] Field of Search ..................................... 424/450, 428; 426/89, 98, 99, 100

[56] References Cited

U.S. PATENT DOCUMENTS 5,139,803  8/1992  Haynes et al. ........................ 426/330.6
5,320,906  6/1994  Eley et al. .............................. 424/450

OTHER PUBLICATIONS

Lecture by Prof. Richard F. Hurrell entitled "Iron Fortification of Infant Cereals".

*Primary Examiner*—Nathan M. Nutter
*Assistant Examiner*—Duc Truong
*Attorney, Agent, or Firm*—Jacobson, Price, Holman & Stern

[57] ABSTRACT

Liposomes comprising an iron (II) source selected from the group consisting of ferrous sulfate, ferrous lactate and ferrous citrate. The iron source is stabilized in aqueous solutions of reducing agents, such as, ascorbic acid and soluble ascorbates, which inhibit oxidation of iron (II) to iron (III) and is microencapsulated. A process by which the liposomes containing the iron (II) source are formed is also provided whereby the iron source is encapsulated into an ingestible form.

The liposomes make it possible to increase the level of bioavailable iron in ingestible substrates.

10 Claims, No Drawings

LIPOSOMES CONTAINING BIOAVAILABLE IRON (II) AND PROCESS FOR OBTAINING THEM

SUMMARY OF THE INVENTION

Herein is proposed an additive to supplement the iron intake, which comprises bioavailable iron (II) in an aqueous medium, encapsulated in liposomes; said medium comprises reducing agents, such as ascorbic acid or its salts, as stabilizers of the reduced state of the iron.

A process is further proposed for the preparation of the liposomes carrying the bioavailable iron starting from the iron (II) and phosphoglycerides, in an aqueous medium.

ANTECEDENTS OF THE INVENTION

The lipidic bilayer structure proper of the biological membranes can also be found in the film casing which constitutes the outer layer of the globular particles generically called "liposomes". These globular particles are vesicles or microscopic sacks, whose size is from 0.01–0.2 microns in diameter, which were discovered in the first half of the decade of the 60s. They result from the spontaneous organization of the molecules of certain lipids of anfiphylic nature in aqueous medium, such as the phospholipids.

The conventional method for the preparation of liposomes implies treating the film deposited by the total evaporation of the solvent of phospholipid solutions (for example, lecithin) with an aqueous medium while stirring energetically (by mechanic or sonic means). Under these conditions, said film disintegrates, the anfiphylic molecules reorder themselves spontaneously in the aqueous medium, forming a dispersion of globules or vesicles of an average diameter determined by the intensity of the agitation or stirring, temperature, etc.

From the reordering of the anfiphylic molecules in the dispersion means, a population of vesicles arises which present themselves preferently as: i) vesicles limited by a casing formed by a double layer of anfiphylic molecules (with a thickness of about 4 manometers) coupled by the ends to non polar tails and with the heads (polars) respectively oriented towards the dispersion means and the encapsulated aqueous means. ii) vesicles whose casing is formed by at least two of said concentric bilayers, separated by a thin laminate from the dispersion means. These major structures are known as unilamellar vesicle, and multilamellar vesicles, respectively.

Said method is not the only one for preparing the mentioned vesicles (liposomes). Other methods have been described, based on the injection in aqueous medium of lipid solutions in very volatile solvents such as freons or the dispersion in said medium of powdered lipids, from the evaporation of dissolved lipids, pulverized over "ad hoc" surfaces, etc.

In general, the population of liposomes obtained is not of a homogeneus diameter. The uniformity required in diverse applications, especially in medicine and cosmetics, can be reached with posterior treatments, by ultrasonic via, and also by filtration with selective pores membrane.

Liposomes have found a broad and ever increasing application for the transport of therapeutic agents in the body, bronchodilators for example; for the transference of generic material in the field of nutrition of vegetables; in the food industry, in the ripening process of cheeses, and in cosmetics (liposomic preparations for skin treatment).

On the other hand, the nutritional requirements related to the contribution of elements which are essential for the development of vital processes, are well known; these elements are called microelements (oligo-elements) mostly transition metals, principally iron, zinc, copper, manganese, molybdenum chromium, cobalt and besides selenium. Iron is found in a solution of 3–4 g., Zn in 1.8 g/70 kg weight and the remainder from 1 to 80 mg.

The corporeal economy of these elements is based on the metabolic reutilization of the same and on the normal intake by ingestion with the food. Where iron is concerned, about 0.6 to 1.5 mg/day are required, whereas the absortion is of the order of 10% as an average on the total content of iron in the diet.

The intestinal absorption rate of iron depends on several factors: nature of the foodstuff: it is lower in the foods of vegetable origin: absorption of iron (formation of insoluble fitates of iron); in the manner of ingestion of the foods, raw of cooked; on the chemical state of the iron: iron is absorbed in its ferrous state and its bioavailability is greater when it is found as Fe-heminic.

Bearing in mind the importance of iron in the synthesis of vital molecules (haemoglobin, mio-haemoglobin, cellular hemines, metabolic enzymes, etc.), the tendency has developed of enriching the diet with iron, and in cases complementing it with other microelements (copper, zinc, etc.) thus enriching bread, cereal preparations, and especially milk, so as to obtain iron bioavailable levels in these foodstuffs compatible with the average iron in the diet.

In practice, the incorporation of iron to the food is carried out by adding inorganic iron salts, for example iron sulfate (II), organic iron as iron lactate or citrate, etc. the absorption of which occurs in a partial manner at intestinal level, in relation to the content of iron in the foods ingested.

THE INVENTION

We have now seen that it is possible to increase the level of bioavailable iron in ingestible substrates, by incorporating to them iron (II) in stabilized aqueous solution with reducing agents which are inhibitors of the oxidation to Fe(III), said solution being microencapsulated in liposomes.

Consequently, an object of the present invention is a process for preparing liposomes containing Fe(II), bioavailable, which comprises forming a homogeneous suspension in water of phosphoglycerides 30–50 g/L; freezing to $-10°$ to $-15°$ and defreezing the formed suspension to ambient temperature, in cycles repeated at least twice, consisting of fast freezing and slow defreezing; incorporating to the homogenized and defrozen suspension, iron (II) in aqueous solution which includes reducing agents capable of inhibiting the oxidation of iron (III); repeating the fast freezing and slow defreezing, and separating the liposomes formed.

Another object of the invention is a process for preparing liposomes containing Fe (II) which comprises forming a solution 30–50 g/L of phosphoglycerides in an organic solvent medium; evaporating the solution until a thin film is formed on the walls of the evaporation receptacle, exempt from solvent; adding in the evaporation receptacle an aqueous solution of Fe(II) which includes reducing agents capable of inhibiting the oxidation to Fe (III), under agitation at ambient temperature, and separating the liposomes formed.

DETAILED DESCRIPTION OF THE INVENTION

The phosphoglycerides which are mentioned to form liposomes containing Fe (II) bioavailable of the present invention, include in a broader aspect the phosphoglycerides whose polar head fraction is with amino-alcohols, such as ethanolamine and choline (ethanolamine phosphoglycerides and choline phosphoglycerides) and/or aminoacids such as serine. Inclusive also the mixtures of phosphoglycerides which are obtained from the fractioning and purification of natural phospholipids known as "lecithin", "cefaline", etc., such as egg or soy lecithin.

The iron (II) microencapsulated in the liposomes of this invention, includes any of the salts, inorganic ferrous salts soluble in water, pharmaceutically acceptable, principally iron sulfate, and also the complexes of salts with anions and organic chelating agents: citrates, lactates and complexes with EDTA.

The liposomes of the present invention include besides a component or biocompatible reducing system capable of inhibiting the oxidation of iron during the elaboration stages and the storage of the liposomes and of the products containing them. Ascorbic acid and the soluble ascorbates are particularly preferred, as well as other biocompatible reducers with appropriate redox potential.

The encapsulation of iron (II) to form the liposomes of the present invention can adopt different operative alternatives. One of them includes the utilization of lecithins of a transition temperature close to 0° C. For example, starting from soy or egg lecithin (with a content of Fosfatidil Colina for example, not less than 90%), at ambient temperature, using a turbine homogenizer and employing lecithin concentrations between 30 and 50 g/L.

One the homogeneous suspension has been obtained, it is rapidly cooled to −10° to −15° C. Next day it is left to defreeze spontaneously and the operation of fast freezing and slow defreezing is repeated. To the suspension obtained is added the solution of ferrous sulfate stabilized with the selected reducer; they are conveniently mixed and are rapidly frozen and spontaneously defrozen. In the end, the Liposomes are separated from the solution of Ferrous Sulfate not microencapsulated by centrifugation.

Another possible operational alternative is to dissolve the phosphoglyceride (soy lecithin, for example) in an appropriate solvent medium. For example:

The lecithin is dissolved (of a transition temperature close to 0° C.) in Chloroform/Methanol 2:1, in the adequate proportion (depending on the Lecithin utilized), to obtain a limpid solution. Preferently, solutions are prepared in which the concentration of lecithin is comprised between 30 and 50 g/L. Later, the solvent is evaporated from the limpid solution formed in a rotating evaporator at reduced pressure (water trumpet blast) until a fine film is obtained on the walls of the receptacle. It is necessary to ascertain that no residue of the organic solvent remain, for which reason it is convenient to connect the receptacle to a vacuum pump (a few microns of pressure) for a few hours.

The next process is to form the Liposomes, adding the solution of Ferrous Sulfate, stabilized with the appropriate reducer, to the previous receptacle, stirring vigorously at ambient temperature, continuing the agitation until there is no lecithin deposited on the walls.

It is convenient to submit the Liposomes suspension to a sonication process in an ultrasonic bath for a few minutes with sequences of 30 sec. of sonication and 30 sec. rest.

Finally, the suspension is allowed to rest during one night at 4° C., before centrifuging to separate the Liposomes.

In the techniques mentioned, the freezing of the lecithin suspensions can be obviated, working with lecithin solutions in organic solvents (methanol/Chloroform already stated), maintaining said solutions at a temperature not inferior to 20° C. below the transition temperature of the lecithin, and the adding of the Ferrous Sulphate solution must rake place at 20° C. above the transition temperature of the Lecithin utilized.

The aqueous microencapsulated solution can be enriched with other microelements, besides iron, such as zinc, copper, and cobalt or mixtures of them.

The liposomes of the present invention are of use for the enrichment of foodstuffs containing bioavailable iron. Particularly for the enrichment of whole or creamless milk, in the preparation of simil-mother's milk and of other milk-products of massive consumption such as yoghurt, cultivated milk, and cheeses in general. Said liposomes have also proven to be useful for increasing the bioavailable iron in diverse sweets and desserts, such as custard, gelatines, etc.

In the following illustrative Example, there is described one of the possible manners of carrying out the invention.

EXAMPLE

To one liter of distilled water at ambient temperature ($\cong 25°$ C.) 40 gr. of lecithin of Soy is added (NC 95 of Natterman Chemie, Germany), finely divided and in small portions, stirring vigorously with a turbine with a deflector, avoiding the incorporation of air during the homogenization process.

One the homogeneous suspension has been obtained (controlled by phase contrast microscopy), it is rapidly frozen in a freezer at −10°, −15° C. and conserved for a night. The next day, the suspension is spontaneously defrozen at ambient temperature ($\cong 25°$ C.) and the process of fast freezing and spontaneous defreezing is repeated.

To 1 L of this suspension is added 1 L of Ferrous Sulfate Heptahydrated solution (alimentary degree) of a concentration of 150 g/L with 10 g/L of Ascorbic Acid, which acts as stabilizer; this is carefully mixed and rapidly frozen to −10°, −15° C. Next day, this is spontaneously defrozen and the Liposomes separated by centrifugation at 8000 g during 2 hours.

A concentrated suspension (approximately 0.51) of liposomes was obtained containing Fe (II) encapsulated sufficient for supplementing milk in a 1/1000 relation (1 L of said suspension with 1000 L of common milk), and carries the concentration of Fe (II) to 15 mg/L in the enriched milk.

Having thus particularly described and determined the nature of the present invention and the manner it has to be carried out, we declare that what is claimed as exclusive property and invention is:

1. Liposomes useful as a source of bioavailable iron which comprises an iron (II) source selected from a group consisting of ferrous sulfate, ferrous lactate and ferrous citrate in an aqueous solution; said iron being microcapsulated and stabilized with ascorbic acid and soluble salts thereof as an inhibitor of iron (II); said liposomes being formed by lecithin phosphoglycerides.

2. Liposomes in accordance with claim 1, characterized by the fact that said lecithin is a lecithin whose transition temperature is of the order of 0° C.

3. Liposomes in accordance with claim 1, characterized by the fact that the lecithin is a lecithin whose transition temperature is higher than 20° C.

4. Liposomes in accordance with claim 1, characterized by the fact that said aqueous solution contains other microelements selected from a group consisting of copper, zinc, cobalt and mixtures thereof.

5. Food products enriched with iron, characterized by the fact that they include liposomes in accordance with claim 1, as an additional source of bioavailable iron.

6. Milk enriched with iron, characterized by the fact that it contains as an additional source of bioavailable iron, liposomes as claimed in claim 1.

7. A process for preparing liposomes according to claim 1, comprising:
   a) forming a homogeneous aqueous suspension of from 30 to 50 g/l of lecithin;
   b) freezing the formed suspension at a temperature of from −10° to −15° C.;
   c) thawing the suspension;
   d) repeating steps (b) and (c) at least twice.
   e) incorporating iron (II) in an aqueous solution with ascorbic acid and soluble salts thereof as an oxidation inhibitor of iron (II) into the homogenized and thawed suspension;
   f) repeating step (d); and
   g) separating the formed liposomes.

8. A process according to claim 1 comprising:
   a) forming a solution in an organic solvent medium containing 30 to 50 grams/l of lecithin;
   b) evaporating said solution to form a thin solvent free layer on the evaporator vessel;
   c) introducing an aqueous iron (II) solution including ascorbic acid and soluble salts thereof as an oxidation inhibitor, into the evaporator vessel, while stirring the solution at room temperature; and
   d) separating the formed liposomes.

9. Process according to claim 4, further comprising adding microelements selected from a group consisting of copper, zinc, cobalt and mixtures thereof.

10. Liposomes according to claim 1 wherein the concentration of iron (II) is at least 15 mg/l.

* * * * *